US009808224B2

(12) United States Patent
Chen et al.

(10) Patent No.: US 9,808,224 B2
(45) Date of Patent: Nov. 7, 2017

(54) METHOD AND SYSTEMS FOR A REMOVABLE TRANSDUCER WITH MEMORY OF AN AUTOMATED BREAST ULTRASOUND SYSTEM

(71) Applicant: General Electric Company, Schenectady, NY (US)

(72) Inventors: Jiayu Chen, Palo Alto, CA (US); Douglas G. Summers, Palo Alto, CA (US)

(73) Assignee: General Electric Company, Schenectady, NY (US)

( * ) Notice: Subject to any disclaimer, the term of this patent is extended or adjusted under 35 U.S.C. 154(b) by 305 days.

(21) Appl. No.: 14/042,571

(22) Filed: Sep. 30, 2013

(65) Prior Publication Data
US 2015/0094589 A1    Apr. 2, 2015

(51) Int. Cl.
| | |
|---|---|
| A61B 8/00 | (2006.01) |
| A61B 8/08 | (2006.01) |
| G01S 15/89 | (2006.01) |
| G01S 7/52 | (2006.01) |

(52) U.S. Cl.
CPC .......... *A61B 8/4488* (2013.01); *A61B 8/0825* (2013.01); *A61B 8/403* (2013.01); *A61B 8/429* (2013.01); *A61B 8/4218* (2013.01); *A61B 8/4461* (2013.01); *A61B 8/4494* (2013.01); *A61B 8/483* (2013.01); *A61B 8/546* (2013.01); *G01S 7/5205* (2013.01); *G01S 7/52079* (2013.01); *G01S 7/52082* (2013.01); *G01S 15/899* (2013.01); *G01S 15/8993* (2013.01)

(58) Field of Classification Search
None
See application file for complete search history.

(56) References Cited

U.S. PATENT DOCUMENTS

| | | | |
|---|---|---|---|
| 5,487,386 A | | 1/1996 | Wakabayashi et al. |
| 5,820,549 A | | 10/1998 | Marian, Jr. |
| 5,989,199 A | * | 11/1999 | Cundari et al. ............... 600/587 |
| 6,270,460 B1 | | 8/2001 | McCartan et al. |
| 6,308,089 B1 | * | 10/2001 | von der Ruhr et al. ...... 600/338 |

(Continued)

FOREIGN PATENT DOCUMENTS

| | | |
|---|---|---|
| WO | 01/39668 A1 | 6/2001 |
| WO | 2004030523 A2 | 4/2004 |

(Continued)

OTHER PUBLICATIONS

Machine Translation of JP 2006-020749, along with original foreign reference. Inventor: Otake Akifumi. Assignee: Aloka Co Ltd. Publication No. JP 2006020749 A (Jan. 26, 2006). Application No. JP 2004200188 A (Jul. 7, 2004). pp. 1-9.*

(Continued)

*Primary Examiner* — James Kish
(74) *Attorney, Agent, or Firm* — McCoy Russell LLP

(57) ABSTRACT

Various methods and systems are provided for a removable transducer module having memory. In one example, a transducer module for an ultrasound imaging system comprises a casing configured to fit into a module receiver of the ultrasound imaging system, an array of transducer elements, and a non-transitory memory configured to store at least one of usage data and specification data for the transducer module.

11 Claims, 8 Drawing Sheets

(56) References Cited

U.S. PATENT DOCUMENTS

| | | |
|---|---|---|
| 6,695,786 B2 | 2/2004 | Wang et al. |
| 8,162,833 B2 | 4/2012 | Zhang et al. |
| 8,184,882 B2 | 5/2012 | Yu et al. |
| 8,272,603 B2 | 9/2012 | Fadler et al. |
| 8,317,702 B2 | 11/2012 | Yu et al. |
| 2002/0038088 A1 | 3/2002 | Imran et al. |
| 2003/0007598 A1 | 1/2003 | Wang et al. |
| 2003/0212327 A1 | 11/2003 | Wang et al. |
| 2004/0002657 A1 | 1/2004 | Marian |
| 2004/0171935 A1 | 9/2004 | Van Creveld et al. |
| 2005/0251035 A1* | 11/2005 | Wong .................. A61B 8/00 600/437 |
| 2006/0241423 A1 | 10/2006 | Anderson et al. |
| 2008/0269613 A1 | 10/2008 | Summers et al. |
| 2009/0043204 A1 | 2/2009 | Pelissier et al. |
| 2009/0088639 A1* | 4/2009 | Maschke .................. 600/443 |
| 2010/0016720 A1* | 1/2010 | Iwasaki .................. A61B 8/00 600/443 |
| 2010/0063396 A1* | 3/2010 | Anderson et al. ............ 600/459 |
| 2010/0256500 A1 | 10/2010 | Anderson et al. |
| 2011/0112405 A1* | 5/2011 | Barthe ................ A45D 44/005 600/459 |
| 2012/0130241 A1 | 5/2012 | Wang et al. |
| 2012/0302887 A1 | 11/2012 | Anderson et al. |
| 2012/0316407 A1* | 12/2012 | Anthony .............. A61B 8/4209 600/301 |
| 2013/0158411 A1* | 6/2013 | Miyasaka .................. 600/472 |
| 2014/0187955 A1* | 7/2014 | Kang ................ A61B 19/5244 600/449 |

FOREIGN PATENT DOCUMENTS

| | | |
|---|---|---|
| WO | 2005/053664 A2 | 6/2005 |
| WO | 2005053664 A2 | 6/2005 |
| WO | 2005104729 A2 | 11/2005 |
| WO | 2005120357 A1 | 12/2005 |
| WO | 2007/014292 A2 | 2/2007 |
| WO | 2007014292 A2 | 2/2007 |
| WO | 2007/130526 A2 | 11/2007 |

OTHER PUBLICATIONS

International Search Report and Written Opinion from Corresponding PCT Application No. PCT/US2014/051407 dated Nov. 19, 2014; 8 pages.

International Search Report and Written Opinion regarding International Application No. PCT/US2014/051407, dated Mar. 4, 2015, 19 pages.

* cited by examiner

METHOD AND SYSTEMS FOR A REMOVABLE TRANSDUCER WITH MEMORY OF AN AUTOMATED BREAST ULTRASOUND SYSTEM

FIELD

Embodiments of the subject matter disclosed herein relate to medical imaging and the facilitation of ultrasonic tissue scanning.

BACKGROUND

Volumetric ultrasound scanning of the breast may be used as a complementary modality for breast cancer screening. Volumetric ultrasound scanning usually involves the movement of an ultrasound transducer relative to a tissue sample and the processing of resultant ultrasound echoes to form a data volume representing at least one acoustic property of the tissue sample. Whereas a conventional two-dimensional x-ray mammogram only detects a summation of the x-ray opacity of individual slices of breast tissue over the entire breast, ultrasound can separately detect the sonographic properties of individual slices of breast tissue, and therefore may allow detection of breast lesions where x-ray mammography alone fails. Further, volumetric ultrasound offers advantages over x-ray mammography in patients with dense breast tissue (e.g., high content of firogladular tissues). Thus, the use of volumetric ultrasound scanning in conjunction with conventional x-ray mammography may increase the early breast cancer detection rate.

In one example, a full-field breast ultrasound (FFBU) scanning apparatus may be used to image breast tissue in one or more planes. One side of an at least partially conformable, substantially taut membrane or film sheet compresses the breast. A transducer translation mechanism maintains an ultrasound transducer in contact with the other side of the film sheet while translating the ultrasound transducer thereacross to scan the breast. Over time, transducers may become degraded and the quality of resulting tissue images may decrease. Degraded transducers may not be serviced or changed out until machine servicing personal may be contacted. This may delay patient treatment and increase costs to the medical providers.

BRIEF DESCRIPTION

In one embodiment, a transducer module for an ultrasound imaging system comprises a casing configured to fit into a module receiver of the ultrasound imaging system, an array of transducer elements, and a non-transitory memory configured to store at least one of usage data and specification data for the transducer module.

In this way, the memory of the transducer module may track usage data such as how many times and how long the transducer has been used for scanning. This information may enable users to determine when a transducer module has reached its service lifetime. Upon reaching the service lifetime, the user may replace the old transducer module with a new transducer module before the old module becomes degraded. As a result, the consistency of image quality and diagnosis of breast cancer may increase.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of a modular transducer system for a full-field breast ultrasound (FFBU) scanning apparatus. X-ray mammography is the most commonly used imaging method for mass breast cancer screening. However, x-ray mammograms only detect a summation of the x-ray opacity of individual slices over the entire breast. Alternatively, ultrasound imaging can separately detect sonographic properties of individual slices of breast tissue, thereby enabling users to detect breast lesions where x-ray mammography alone may fail.

In one example, volumetric ultrasound scanning of the breast may be used as a complementary modality for breast cancer screening. Volumetric ultrasound scanning may include moving an ultrasound transducer relative to a tissue sample and then processing the resultant ultrasound echoes to form a data volume representing at least one acoustic property of the tissue sample. Another well-known shortcoming of x-ray mammography practice is found in the case of dense-breasted women, including patients with high content of fibroglandular tissues in their breasts. Because fibroglandular tissues have higher x-ray absorption than the surrounding fatty tissues, portions of breasts with high fibroglandular tissue content are not well penetrated by x-rays and thus the resulting mammograms contain reduced information in areas where fibroglandular tissues reside. Thus, the use of volumetric ultrasound scanning in conjunction with conventional x-ray mammography may increase the early breast cancer detection rate.

Figure 1:
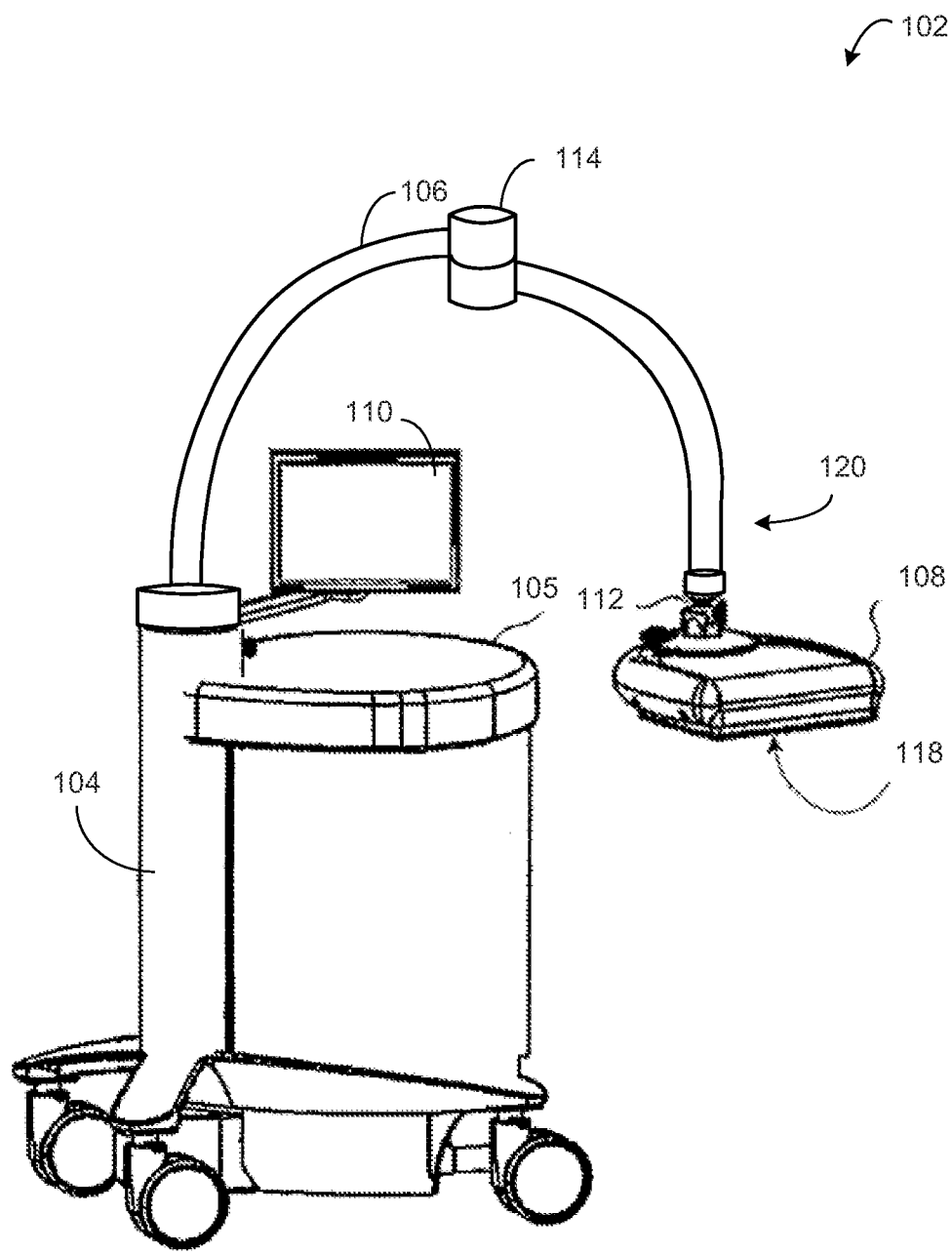
FIG. 1 shows a perspective view of a scanning apparatus according to an embodiment of the invention.
Figure 2:
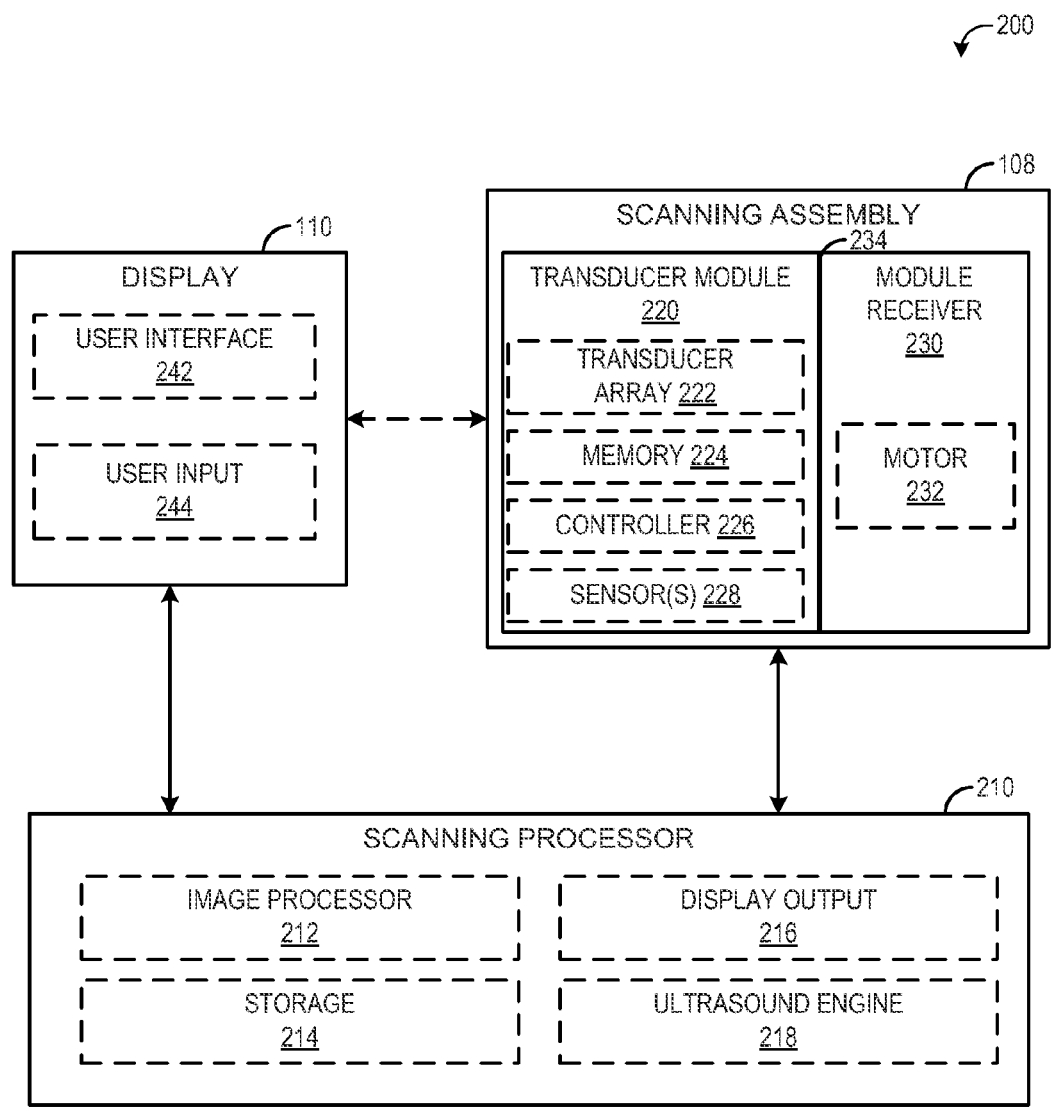
FIG. 2 shows a schematic of various system components of a scanning apparatus according to an embodiment of the invention.
Figure 3:
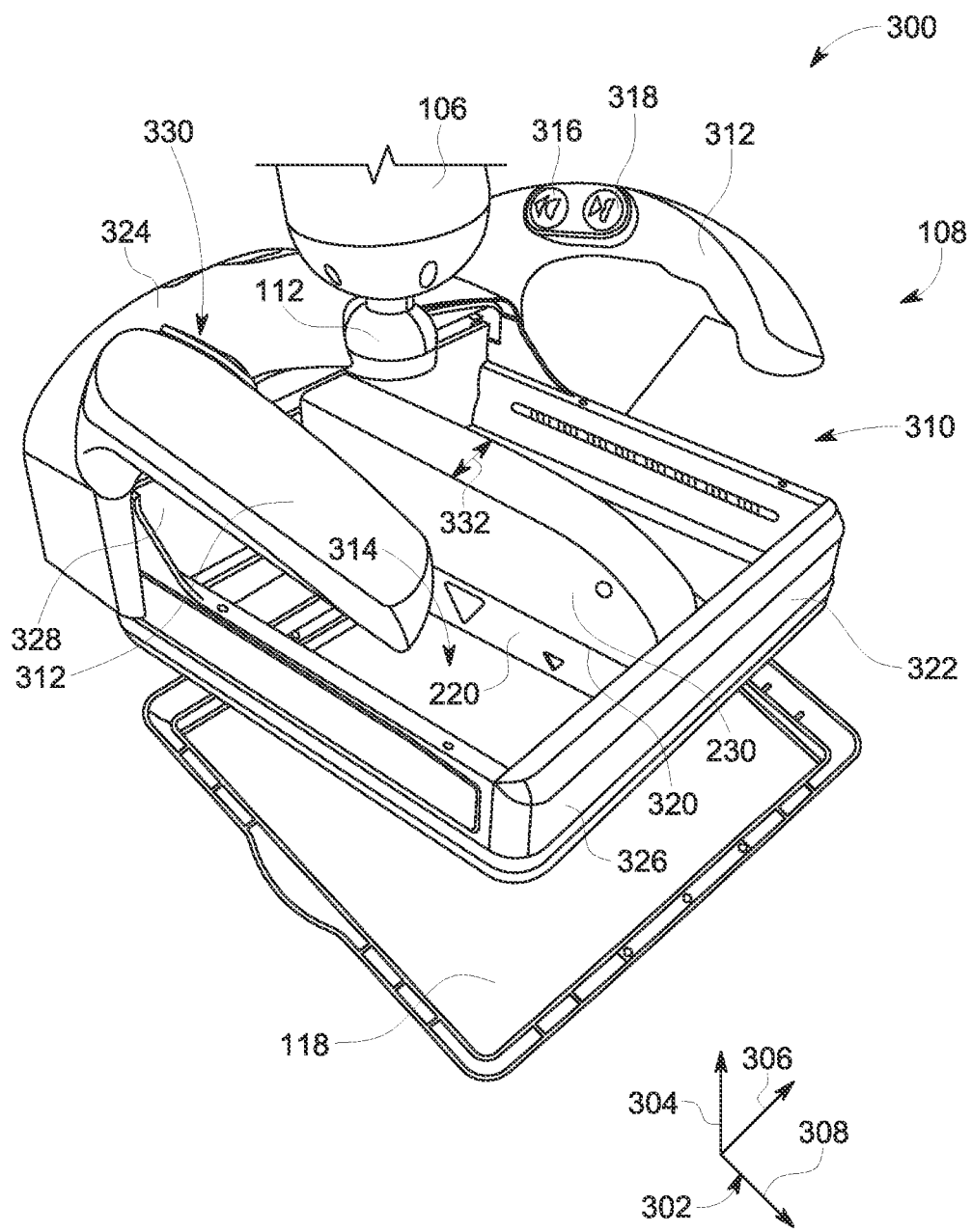
FIG. 3 shows a scanning assembly of a scanning apparatus according to an embodiment of the invention.
Figure 4:
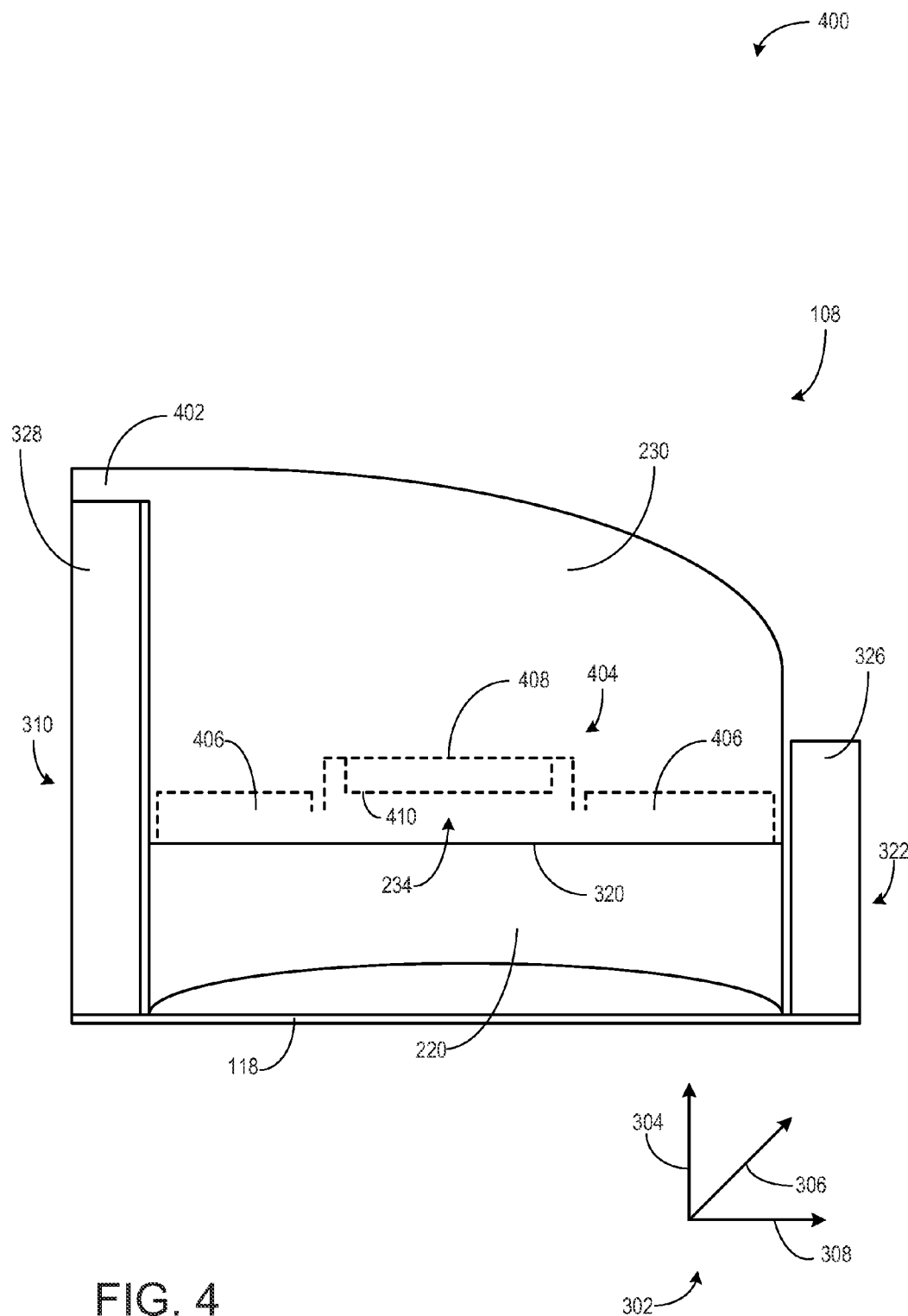
FIG. 4 shows a cross-section of a scanning assembly of a scanning apparatus according to an embodiment of the invention.

In one example, a full-field breast ultrasound (FFBU) scanning apparatus, such as the FFBU scanning apparatus depicted in FIGS. 1-2, compresses a breast in a generally chestward or head-on direction and ultrasonically scans the breast. In another example, the FFBU scanning apparatus may compress a breast along planes such as the craniocaudal (CC) plane, the mediolateral oblique (MLO) plane, or the like. A compression/scanning assembly of the FFBU scanning apparatus may include an at least partially conformable, substantially taut membrane or film sheet, an ultrasound transducer, and a transducer translation mechanism. One side of the taut membrane or film sheet compresses the breast. The transducer translation mechanism maintains the ultrasound transducer in contact with the other side of the film sheet while translating the ultrasound transducer thereacross to scan the breast. An example the compression/scanning assembly is shown at FIGS. 3-4.

Over time, the functionality of the ultrasound transducer may degrade and/or the ultrasound transducer may break. However, the ultrasound transducer may be mechanically and electrically coupled within the FFBU scanning apparatus such that it cannot be removed by an end user (e.g., ultrasound technician or physician). As a result, the FFBU scanning apparatus may be unusable until a trained service operator is able to service and/or swap out the degraded ultrasound transducer for a non-degraded ultrasound transducer. While awaiting servicing, the FFBU scanning apparatus may not be used to diagnose patients, thereby delaying patient diagnosis and increasing costs to medical providers.

It may be desirable to exchange the ultrasound transducer installed within the FFBU scanning apparatus for additional reasons other than degradation. For example, a FFBU scanning apparatus may scan all patients with the same transducer despite differing breast anatomy among patients. However, volumetric breast scans may be highly patient-specific processes due to the wide variety of breast sizes, shapes, and densities. Instead of using one standard ultrasound transducer for nearly all patients, different ultrasound transducers with varying shapes, sizes, or imaging characteristics may be used to image different patients based on individual patient anatomy. A modular transducer system, such as the modular transducer system shown in FIGS. 3-6B, may allow for different ultrasound transducers to be quickly and easily exchanged from patient to patient without requiring a service operator. Choosing an ultrasound transducer based on patient anatomy may allow for increased image quality and therefore an increased rate of early detection of breast cancer.

Although several examples herein are presented in the particular context of human breast ultrasound, it is to be appreciated that the present teachings are broadly applicable for facilitating ultrasonic scanning of any externally accessible human or animal body part (e.g., abdomen, legs, feet, arms, neck, etc.). Moreover, although several examples herein are presented in the particular context of mechanized scanning (i.e., in which the ultrasound transducer is moved by a robot arm or other automated or semi-automated mechanism), it is to be appreciated that one or more aspects of the present teachings can be advantageously applied in a handheld scanning context.

FIG. 1 illustrates a perspective view of a full-field breast ultrasound (FFBU) scanning apparatus 102 according to an embodiment, comprising a frame 104 that contains an ultrasound processor, a movable and adjustable support arm 106 (e.g., adjustable arm) including a hinge joint 114, a compression/scanning assembly 108 connected to the adjustable arm 106 via a ball-and-socket connector (e.g., ball joint) 112, and a display 110 connected to the frame 104. The display 110 is coupled to the frame 104 at an interface where the adjustable arm 106 enters into the frame 104. As a result of being directly coupled to the frame 104 and not to the adjustable arm 106, the display 110 does not affect a weight of the adjustable arm 106 and a counterbalance mechanism of the adjustable arm 106. In one example, the display 110 is rotatable in a horizontal and lateral direction (e.g., rotatable around a central axis of the frame 104), but not vertically movable. In an alternate example, the display 110 may also be vertically movable. While FIG. 1 depicts the display 110 coupled to the frame 104, in other examples the display 110 may be coupled to a different component of the scanning apparatus 102, such as coupled to the ultrasound processor housing 105, or located remotely from the scanning apparatus 102.

In one embodiment, the adjustable arm 106 is configured and adapted such that the compression/scanning assembly 108 is either (i) neutrally buoyant in space, or (ii) has a light net downward weight (e.g., 1-2 kg) for breast compression, while allowing for easy user manipulation. In alternate embodiments, the adjustable arm 106 is configured such that the compression/scanning assembly 108 is neutrally buoyant in space during positioning the scanner on the patient's tissue. Then, after positioning the compression/scanning assembly 108, internal components of the adjustable arm 106 may be adjusted to apply a desired downward weight for breast compression and increased image quality. In one example, the downward weight (e.g., force) may be in a range of 2-11 kg.

As introduced above, the adjustable arm 106 includes a hinge joint 114. The hinge joint 114 bisects the adjustable arm 106 into a first arm portion and a second arm portion. The first arm portion is coupled to the compression/scanning assembly 108 and the second arm portion is coupled to the frame 104. The hinge joint 114 allows the second arm portion to rotate relative to the second arm portion and the frame 104. For example, the hinge joint 114 allows the compression/scanning assembly 108 to translate laterally and horizontally, but not vertically, with respect to the second arm portion and the frame 104. In this way, the compression/scanning assembly 108 may rotate toward or away from the frame 104. However, the hinge joint 114 is configured to allow the entire adjustable arm 106 (e.g., the first arm portion and the second arm portion) to move vertically together as one piece (e.g., translate upwards and downwards with the frame 104).

The compression/scanning assembly 108 comprises an at least partially conformable membrane 118 in a substantially taut state for compressing a breast, the membrane 118 having a bottom surface contacting the breast while a transducer is swept across a top surface thereof to scan the breast. In one example, the membrane is a taut fabric sheet. Optionally, the adjustable arm 106 may comprise potentiometers (not shown) to allow position and orientation sensing for the compression/scanning assembly 108, or other types of position and orientation sensing (e.g., gyroscopic, magnetic, optical, radio frequency (RF)) can be used. Within frame 104 may be provided a fully functional ultrasound engine for driving an ultrasound transducer and generating volumetric breast ultrasound data from the scans in conjunction with the associated position and orientation information. The volumetric scan data can be transferred to another computer system for further processing using any of a variety of data transfer methods known in the art. A general purpose computer, which can be implemented on the same computer as the ultrasound engine, is also provided for general user interfacing and system control. The general purpose computer can be a self-contained stand-alone unit, or can be remotely controlled, configured, and/or monitored by a remote station connected across a network.

FIG. 2 is a block diagram 200 schematically illustrating various system components of the scanning apparatus 102, including the scanning assembly 108, display 110, and a scanning processor 210. Scanning processor 210 may be included within frame 104 of the scanning apparatus 102 in one example. As illustrated in the embodiment of FIG. 2, the scanning assembly 108, display 110, and scanning processor 210 are separate components in communication with each other; however, in some embodiments one or more of the components may be integrated (e.g., the display and scanning processor may be included in a single component).

Referring first to the scanning assembly 108, it comprises a transducer module 220 connected to a module receiver 230. As will be explained in more detail below with respect to FIGS. 3-4, the module receiver 230 may be positioned within a housing (attached to the arm 106 of the scanning apparatus, for example) that is configured to remain stationary during scanning, while the module receiver 230 is configured to translate with respect to the housing during scanning. In order to automatically translate with respect to the housing during scanning, the module receiver includes a motor 232 activated by the scanning processor 210, as explained below.

The transducer module 220 comprises a transducer array 222 of transducer elements, such as piezoelectric elements, that convert electrical energy into ultrasound waves and then detect the reflected ultrasound waves. The transducer module 220 is configured to be removably coupled with the module receiver 230 via a connection 234. The connection 234 may include complementary connectors on the transducer module and module receiver (e.g., a first connector on the transducer module that is configured to connect with a second connector on the module receiver) in order to establish both a mechanical connection and an electrical connection between the module receiver and the transducer module.

The transducer module 220 may further include a memory 224. Memory 224 may be a non-transitory memory configured to store various parameters of the transducer module 220, such as transducer usage data (e.g., number of scans performed, total amount of time spent scanning, etc.), as well as specification data of the transducer (e.g., number of transducer array elements, array geometry, etc.) and/or identifying information of the transducer module 220, such as a serial number of the transducer module. Memory 224 may include removable and/or permanent devices, and may include optical memory, semiconductor memory, and/or magnetic memory, among others. Memory 224 may include volatile, nonvolatile, dynamic, static, read/write, read-only, random-access, sequential-access, and/or additional memory. In an example, memory 224 may include RAM. Additionally or alternatively, memory 224 may include EEPROM.

Memory 224 may store non-transitory instructions executable by a controller or processor, such as controller 226, to carry out one or more methods or routines as described herein below. Controller 226 may receive output from various sensors 228 of the transducer module 220 and trigger actuation of one or more actuators and/or communicate with one or more components in response to the sensor output. As will be described in more detail below with reference to FIGS. 6A-B, sensors 228 may include one or more pressure sensors and/or one or more temperature sensors. During scanning, the pressure across the scanning assembly 108 may be measured by the pressure sensors, and if the pressure distribution across the transducer module is not equal, a user may be notified (via user interface 242 of display 110, for example) to reposition the scanning assembly 108. Further, in some embodiments, to initiate scanning, motor 232 may be activated via a signal from controller 226. However, in other embodiments, motor 232 may be activated via a signal from a separate scanning processor 210, explained below.

Scanning assembly 108 may be in communication with scanning processor 210, to send raw scanning data to an image processor, for example. Additionally, data stored in memory 224 and/or output from sensors 228 may be sent to scanning processor 210 in some examples. Further, various actions of the scanning assembly 108 (e.g., translation of the module receiver 230, activation of the transducer elements, etc.) may be initiated in response to signals from the scanning processor 210. Scanning assembly 108 may optionally communicate with display 110, in order to notify a user to reposition the scanning assembly, as explained above, or to receive information from a user (via user input 244), for example.

Turning now to scanning processor 210, it includes an image processor 212, storage 214, display output 216, and ultrasound engine 218. Ultrasound engine 218 may drive activation of the transducer elements of the transducer array 222 of transducer module 220 and, in some embodiments, may activate motor 232. Further, ultrasound engine 218 may receive raw image data (e.g., ultrasound echoes) from the scanning assembly 108. The raw image data may be sent to image processor 212 and/or to a remote processor (via a network, for example) and processed to form a displayable image of the tissue sample. It is to be understood that the image processor 212 may be included with the ultrasound engine 218 in some embodiments.

Information may be communicated from the ultrasound engine 218 and/or image processor 212 to a user of the scanning apparatus 102 via the display output 216 of the scanning processor 210. In one example, the user of the scanning apparatus may include an ultrasound technician, nurse, or physician such as a radiologist. For example, processed images of the scanned tissue may be sent to the display 110 via the display output 216. In another example, information relating to parameters of the scan, such as the progress of the scan, may be sent to the display 110 via the display output 216. The display 110 may include a user interface 242 configured to display images or other information to a user. Further, user interface 242 may be configured to receive input from a user (such as through user input 244) and send the input to the scanning processor 210. User input 244 may be a touch screen of the display 110 in one example. However, other types of user input mechanisms are possible, such as a mouse, keyboard, etc.

Scanning processor 210 may further include storage 214. Similar to memory 224, storage 214 may include removable and/or permanent devices, and may include optical memory, semiconductor memory, and/or magnetic memory, among others. Storage 214 may include volatile, nonvolatile, dynamic, static, read/write, read-only, random-access, sequential-access, and/or additional memory. Storage 214 may store non-transitory instructions executable by a controller or processor, such as ultrasound engine 218 or image processor 212, to carry out one or more methods or routines as described herein below. Storage 214 may store raw image data received from the scanning assembly 108, processed image data received from image processor 212 or a remote processor, and/or additional information.

Figure 5:
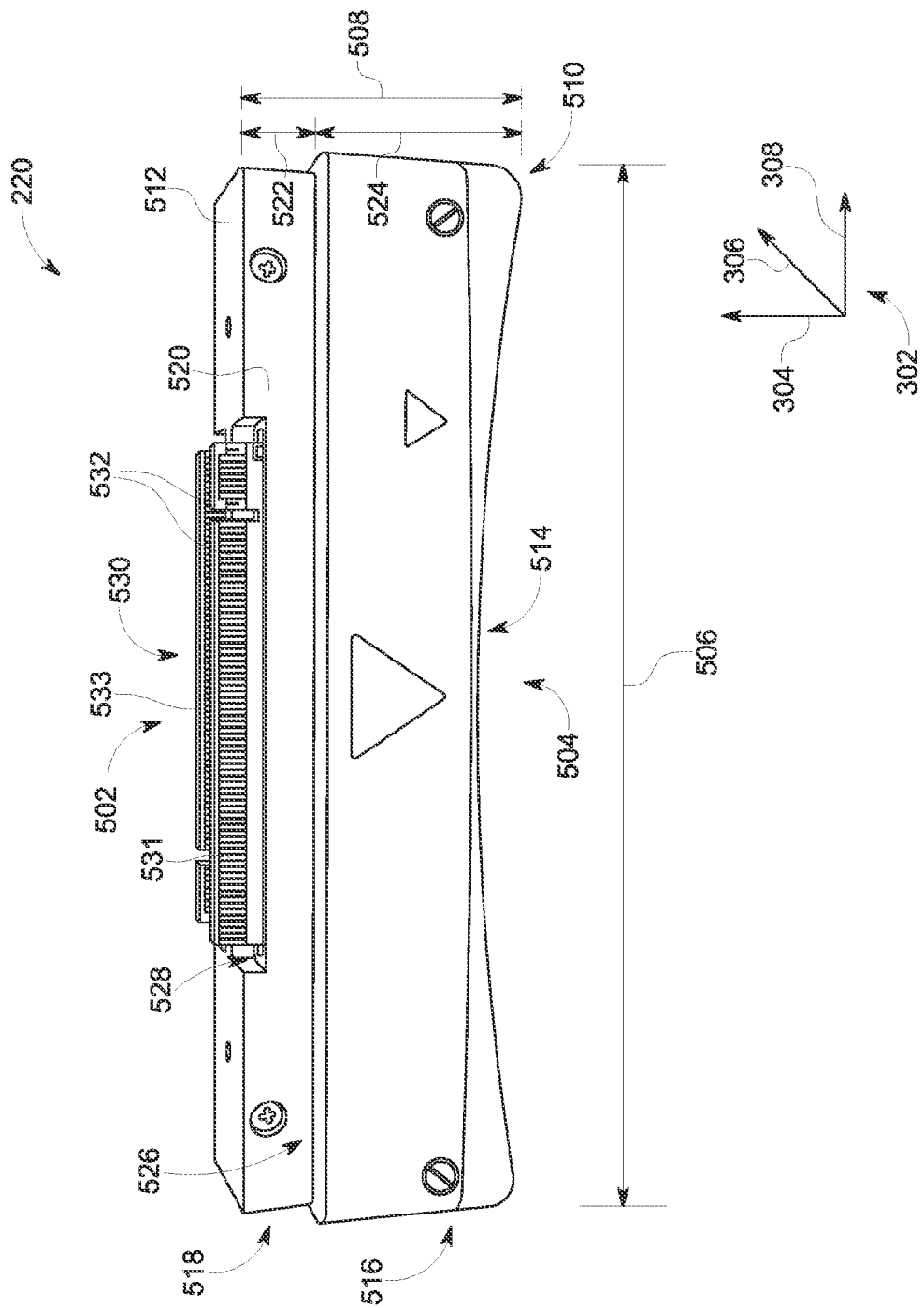
FIG. 5 shows a transducer module of a scanning assembly of a scanning apparatus according to an embodiment of the invention.

FIGS. 3-5 show components of the scanning assembly 108 of the scanning apparatus 102 described above with reference to FIGS. 1-2. Specifically, FIG. 3 shows a schematic 300 of an isometric view of the scanning assembly 108 coupled to the adjustable arm 106. The schematic 300 includes a coordinate system 302 including a vertical axis 304, horizontal axis 306, and a lateral axis 308. FIG. 4 shows a cross-sectional view 400 of the scanning assembly 108. The cross-sectional view 400 is taken in a plane defined by the vertical axis 304 and the lateral axis 308. FIG. 5 shows one embodiment of a transducer module 220 coupleable to the scanning assembly 108.

As shown in FIG. 3, the scanning assembly 108 includes a housing 310, the transducer module 220, and the module receiver 230. The housing 310 includes a frame 322 and a handle portion 324, the handle portion including two handles 312. The two handles 312 are opposite one another across a lateral axis of the scanning assembly 108, the lateral axis centered at the adjustable arm 106 and defined with respect to the lateral axis 308. The frame 322 is rectangular-shaped with an interior perimeter of the frame 322 defining an opening 314. The opening 314 provides a space (e.g., void volume) for translating the module receiver 230 and the transducer module 220 during a scanning procedure. In another example, the frame 322 may be another shape, such as square with a square-shaping opening 314. Additionally, the frame 322 has a thickness defined between the interior perimeter and an exterior perimeter of the frame 322.

The frame 322 includes four sets of side walls (e.g., the set including an interior side wall and an exterior side wall, the interior side walls defining the opening 314). Specifically, the frame 322 includes a front side wall 326 and a back side wall 328, the back side wall 328 directly coupled to the handle portion 324 of the housing 310 and the front side wall 326 opposite the back side wall 328 with respect to the horizontal axis 306. The frame 322 further includes a right side wall and a left side wall, the respective side walls opposite from one another and both in a plane defined by the vertical axis 304 and the lateral axis 308.

The frame 322 of the housing 310 further includes a top side and a bottom side, the top side and bottom side defined relative to the vertical axis 304. The top side faces the adjustable arm 106. A membrane 118 is disposed across the opening 314. More specifically, the membrane 118 is coupled to the bottom side of the frame 322. In one example, the membrane 118 is a membranous sheet maintained taut across the opening 314. The membrane 118 may be a flexible but non-stretchable material that is thin, water-resistant, durable, highly acoustically transparent, chemically resistant, and/or biocompatible. As discussed above, the bottom surface of the membrane 118 may contact a tissue (e.g., such as a breast) during scanning and a top surface of the membrane 118 may at least partially contact the transducer module 220 during scanning. As shown in FIG. 3, the membrane 118 includes a hard-shell clamping portion around a perimeter of the membrane. The clamping portion couples to the bottom side of the frame 322. In one example, the clamping portion may snap to a lip on the bottom side of the frame 322 of the housing 310 such that membrane 118 does not become uncoupled during scanning but is still removably coupled to the frame 322.

The handle portion 324 of the housing 310 includes two handles 312 for moving the scanning assembly 108 in space and positioning the scanning assembly 108 on a tissue (e.g., on a patient). In alternate embodiments, the housing 310 may not include handles 312. In one example, the handles 312 may be formed as one piece with the frame 322 of the housing 310. In another example, the handles 312 and the frame 322 may be formed separately and then mechanically coupled together to form the entire housing 310 of the scanning assembly 108.

As shown in FIG. 3, the scanning assembly 108 is coupled to the adjustable arm 106 through a ball joint 112 (e.g., ball-and-socket connector). Specifically, a top, domed portion of the handle portion 324 is coupled to the ball joint 112. The top portion of the handle portion 324 includes a concave depression forming a socket which a ball of the ball joint 112 fits into. The ball joint 112 is moveable in multiple directions. For example, the ball joint 112 provides rotational movement of the scanning assembly relative to the adjustable arm 106. The ball joint 112 includes a locking mechanism for locking the ball joint 112 in place and thereby maintaining the scanning assembly 108 stationary relative to the adjustable arm 106.

Additionally, as shown in FIG. 3, the handles 312 of the handle portion 324 include buttons for controlling scanning and adjusting the scanning assembly 108. Specifically, a first handle of the handles 312 includes a first weight adjustment button 316 and a second weight adjustment button 318. The first weight adjustment button 316 may decrease a load applied to the scanning assembly 108 from the adjustable arm 106. The second weight adjustment button 318 may increase the load applied to the scanning assembly 108 from the adjustable arm 106. Increasing the load applied to the scanning assembly 108 may increase an amount of pressure and compression applied to the tissue on which the scanning assembly 108 is placed. In one example, increasing the load may compress the tissue, such as a breast, of a patient. In this way, varying amounts of pressure (e.g., load) may be applied consistently with the scanning assembly 108 during scanning in order to obtain a quality image with the transducer module 220.

Before a scanning procedure, a user (e.g., ultrasound technician or physician) may position the scanning assembly 108 on a patient or tissue. Once the scanning assembly 108 is positioned correctly, the user may adjust the weight of the scanning assembly 108 on the patient (e.g., adjust the amount of compression) using the first weight adjustment button 316 and/or the second weight adjustment button 318. A user may then initiate a scanning procedure with additional controls on the handle portion 324 of the housing 310. For example, as shown in FIG. 3, a second handle of the handles 312 includes two additional buttons 330 (not individually shown). The two additional buttons 330 may include a first button to initiate scanning (e.g., once the scanning assembly has been placed on the tissue/patient and the amount of compression has been selected) and a second button to stop scanning. In one example, upon selecting the first button, the ball joint 112 may lock, thereby stopping lateral and horizontal movement of the scanning assembly 108.

The module receiver 230 is positioned within the housing 310. Specifically, the module receiver 230 is mechanically coupled to a first end of the housing 310 at the back side wall 328 of the frame 322, the first end closer to the adjustable arm 106 than a second end of the housing 310. The second end of the housing 310 is at the front side wall 326 of the frame 322. In one example, the module receiver 230 is coupled to the first end via a protrusion of the module receiver 230, the protrusion coupled to a motor (e.g., motor 232 described with reference to FIG. 2 above) of the module receiver 230. The protrusion of the module receiver 230 is better seen in FIG. 4, discussed further below.

As described above, the housing 310 is configured to remain stationary during scanning. In other words, upon adjusting a weight applied to the scanning assembly 108 through the adjustable arm 106 and then locking the ball joint 112, the housing 310 may remain in a stationary position without translating in the horizontal or lateral directions. However, the housing 310 may still translate vertically with vertical movement of the adjustable arm 106.

Conversely, the module receiver 230 is configured to translate with respect to the housing 310 during scanning. As shown in FIG. 3, the module receiver 230 translates horizontally, along the horizontal axis 306, with respect to the housing 310. The motor of the module receiver 230 may slide the module receiver 230 along a top surface of the first end of the housing 310 (as seen in FIG. 4, discussed below).

The transducer module 220 is removably coupled with the module receiver 230. As a result, during scanning, the transducer module 220 translates horizontally with the module receiver 230. During scanning transducer module 220 sweeps horizontally across the breast under motor control of the module receiver 230 while a contact surface of the transducer module 220 is in contact with the membrane 118. The transducer module 220 and the module receiver 230 are coupled together at a module interface 320. The module receiver 230 has a width 332 which is the same as a width of the transducer module 220. In alternate embodiments, the width 332 of the module receiver may not be the same as the width of the transducer module 220. The module interface 320 is shown in greater detail at FIG. 4. As discussed with reference to FIG. 4, the module interface 320 includes a connection 234 between the transducer module 220 and the module receiver 230, the connection 234 including a mechanical and electrical connection.

Turning now to FIG. 4, a cross-section of the scanning assembly 108 shows the module receiver 230 coupled to the housing 310 and the module receiver 230 coupled to the transducer module 220 at the module interface 320. As describe above, a protrusion 402 of the module receiver 230 is coupled to the motor (not shown) of the module receiver 230. The protrusion 402 extends across the top surface of the back side wall 328 of the frame 322 of the housing 310. In one example, a small space may be present between the protrusion 402 and the top surface to allow sliding movement of the protrusion 402 along a length of the top surface (e.g., in a lateral direction). As shown in FIG. 4, the module receiver 230 does not contact an interior surface of the back side wall 328 or the front side wall 326 in order to allow the module receiver 230 to translate within the housing 310. Additionally, FIG. 4 shows the membrane 118 extending across a width of the housing 310. The membrane 118 is coupled to the bottom side of the frame 322.

As discussed above, the transducer module 220 is removably coupled to the module receiver 230 at the module interface 320. The module interface 320 includes the connection 234 between the module receiver 230 and the transducer module 220, the connection 234 including a mechanical connection and an electric connection. FIG. 5 shows an example transducer module 220 that is configured to be removably coupled with the module receiver 230. As shown in FIG. 5, the transducer module 220 includes a first end 502 and a second end 504. The first end 502 may be a top end and the second end 504 may be a bottom end with respect to the vertical axis 304 and a tissue on which the scanning assembly 108 is placed. The second end 504 contacts the membrane 118 during scanning and is the end proximate to the tissue being scanned (e.g., the second end 504 is closer to the patient than the first end 502).

Figure 6A:
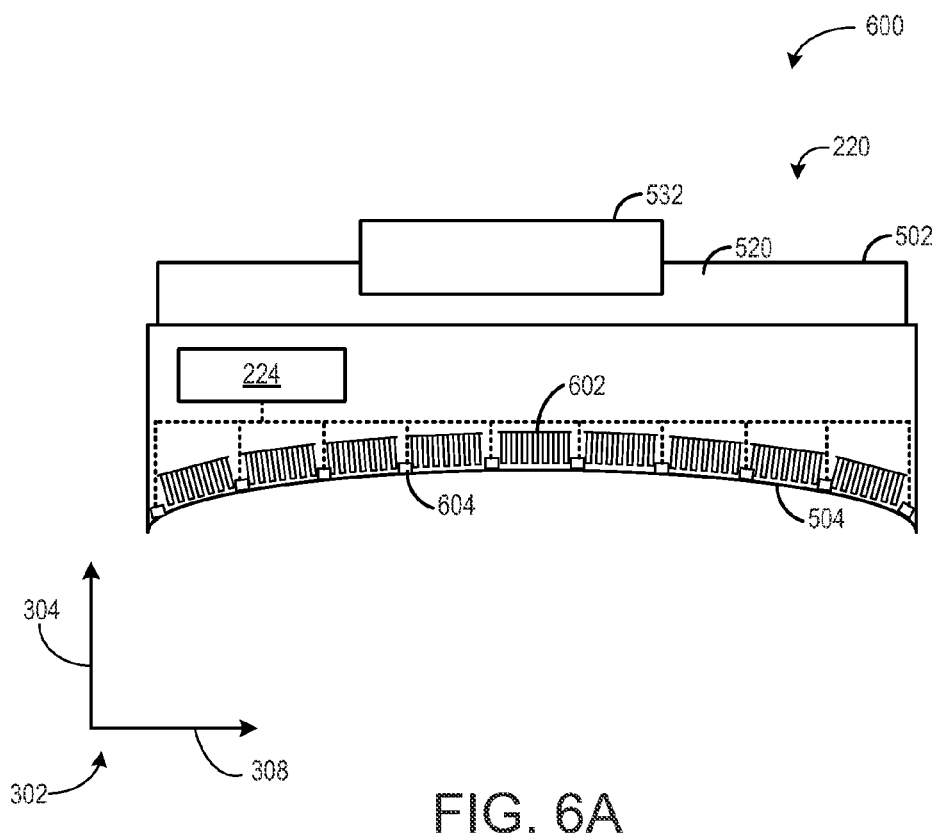
FIGS. 6A-6B show cross-sections of a transducer module of a scanning assembly of a scanning apparatus according to an embodiment of the invention.
Figure 6B:
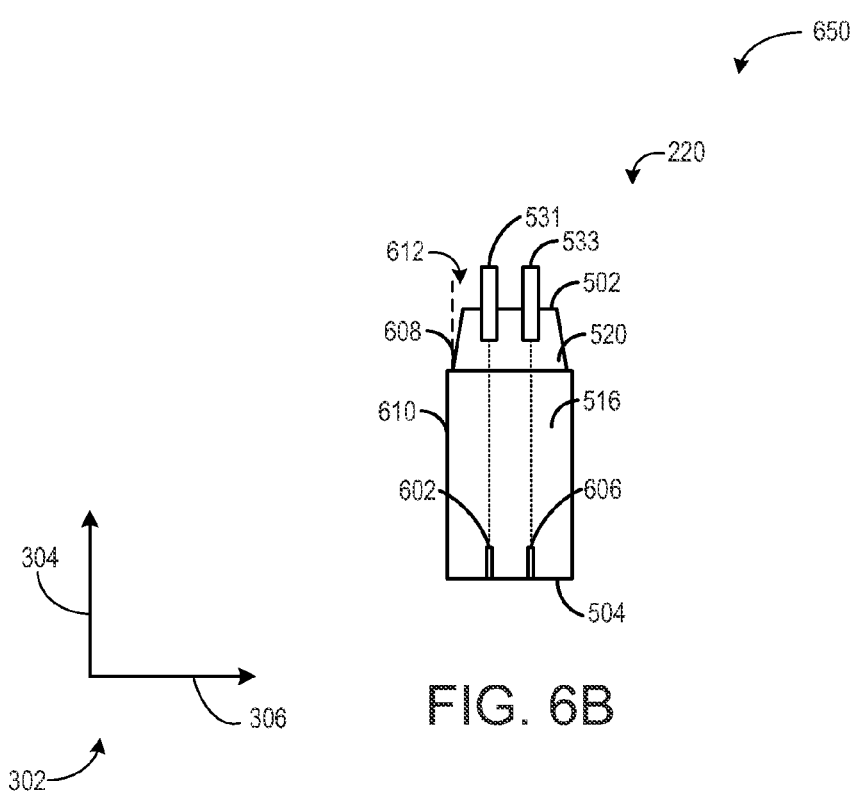

The second end 504 includes a transducer array of transducer elements, as shown at FIGS. 6A and 6B described further below. In one example, the transducer module 220 is a linear array transducer comprising 768 piezoelectric elements. In alternate embodiments, the transducer module 220 may include more or less than 768 transducer elements. In one example, an operating frequency of the transducer array is in a range from 2 MHz to 15 MHz. In another example, the operating frequency range may be from 6 MHz to 10 MHz. In yet another example, the operating frequency may be 7.5 MHz. As described further below, a central frequency (e.g., center frequency or operating frequency) of the transducer array may differ among different transducer modules 220. The second end 504 of the transducer module 220 may also include mechanical focusing elements, such as acoustic lenses, for focusing the ultrasound waves. The transducer elements of the transducer array may be spaced along a length 506 of the transducer module 220, as shown in greater detail at FIG. 6A, described further below.

The length 506 of the transducer module 220 is in a range from approximately 10 cm to 20 cm. In one example, the length 506 of the transducer module 220 is 15 cm. In another example, the length 506 of the transducer module is 18 cm. As described further below, different transducer modules 220 may have different lengths for differently sized patients and based on a size of the target tissue area for scanning. For example, the length 506 may be sized in order to allow imaging of a breast in a single horizontal sweep. However, in other embodiments, multiple shorter transducer modules may be placed end-to-end to achieve a similar result.

Additionally, the transducer module 220 has an external width (e.g., thickness). The external width of the transducer module 220 is the same as the width 332 of the module receiver 230, as shown in FIG. 3. As a result, when coupled together (as best seen in FIG. 3), the transducer module 220 and the module receiver 230 may form a probe assembly with a constant width (e.g., thickness). Returning to FIG. 5, the transducer module 220 also has a total height 508, the total height 508 defined between a base 510 and a top surface 512 of a first protrusion 520 of the transducer module 220.

As shown in FIGS. 4-5, the contact surface of the transducer module 220 at the second end 504 is curved. As a result, the transducer array may also be curved. However, in other examples the transducer array may not be curved and mechanical focusing elements may be used to focus the sound waves. The contact surface of the second end 504 has a curvature radius 514. As discussed further below, the curvature radius 514 of different transducer modules 220 may be different, thereby providing transducer modules with varying amounts of curvature. For example, a first transducer module 220 may have a first curvature radius 514 and a second transducer module may have a second curvature radius 514, the first curvature radius 514 greater than the second curvature radius 514. In some embodiments, a transducer module may have a curvature radius 514 of substantially zero such that the contact surface of the second end 504 is substantially flat. As discussed further below, the curvature radius 514 may be based on a patient's anatomy or tissue contour (e.g., convexity).

The transducer module 220 has an external portion 516 proximate to the second end 504 and an internal portion 518 proximate to the first end 502. The external portion 516 comprises a hard casing (e.g., plastic) and the contact surface. The internal portion 518 is positioned inside the module receiver such that it is not exposed when assembled in the scanning assembly 108, as shown in FIG. 3. Further, the internal portion 518 includes a first protrusion 520 (e.g., first internal protrusion) and a second protrusion 530 (e.g., second internal protrusion). The first protrusion 520 is a rectangular step extending outwardly (in a vertical direction defined with respect to the vertical axis 304) from the external portion 516. As shown in FIG. 5, the rectangular-shaped first protrusion 520 includes rounded edges. The first protrusion 520 has a smaller width and length than the external portion 516 of the transducer module 220. As such, the external portion 516 includes a lip surrounding the internal portion 518. The lip and the first protrusion 520 may form a first recess 526 of the transducer module 220, the first recess 526 extending around a perimeter of the transducer module 220. In one example, the module receiver 230 may include a complementary protrusion that mates with face-sharing contact with the first recess 526. Additionally, the first protrusion 520 may be tapered, as further shown at FIG. 6B.

As shown in FIG. 5, the internal portion 518 is centered along the width and length 506 of the transducer module 220. Additionally, the first protrusion 520 includes a first height 522 which is a portion of the total height 508 of the transducer module 220. The external portion 516 includes a second height 524 which is also a portion of the total height 508. Together, the first height 522 and the second height 524 equal the total height 508. As shown in FIG. 5, the first height 522 is smaller than the second height 524. However, in alternate embodiments, the first height 522 may be the same as the second height 524 or the first height 522 may be larger than the second height 524.

The internal portion 518 includes a second recess 528. The second recess 528 may include two depressions (a first of the depressions is shown in FIG. 5 with the other depression hidden behind the first). The depressions are depressed from a top surface 512 of the first protrusion 520 and into the first protrusion 520 (e.g., toward the second end 504). The depressions of the recess 528 are separated by a thin, central portion of the first protrusion 520. As such, the two depressions of the recess 528 are symmetrical and opposite one another with respect to a central, lateral axis of the transducer module 220.

The second protrusion 530 includes a second standard electrical connector 532, such as a PCI connector. The second standard electrical connector 532 includes two separate electrical connectors, each of the electrical connectors positioned within each of the depressions of the second recess 528. Each of the electrical connectors of the second standard electrical connector 532 may be PCI connectors (e.g., PCI cards). For example, the second standard electrical connector 532 includes a first PCI connector 531 and a second PCI connector 533. The second standard electrical connector 532 is positioned within the second recess 528. In another embodiment, the second standard electrical connector 532 may be a different type of electrical connector such as a serial ATA (SATA).

As shown in FIG. 5, the first PCI connector 531 includes two sections, one longer and one shorter section. The second PCI connector 533 also includes two sections, one longer and one shorter section. However, the longer and shorter sections of the second PCI connector 533 are reversed from the first PCI connector 531. Thus, the first PCI connector 531 and the second PCI connector 533 are reversed and parallel to one another. Specifically, the two PCI connectors 531 and 533 have reverse symmetry with one another such that the transducer module 220 may be inserted into the module receiver 230 in two different orientations, the two different orientations offset from each other by 180 degrees. The longer and shorter sections may provide for PCI cards with a 32 or 64 bit orientation with different voltages.

Further, the multiple parallel rows of PCI connectors of the second standard electrical connector 532 may correspond to multiple parallel rows of transducer elements in the transducer array, as shown at FIG. 6B.

Returning to FIG. 4, the module interface 320 between the transducer module 220 described above with regard to FIG. 5 and the module receiver 230 is shown. The module receiver 230 and the transducer module 220 include complementary connections. The complementary connections include a complementary mechanical connection and a complementary electrical connection. The complementary mechanical connection allows the transducer module 220 to be removably coupled to the module receiver 230 such that the transducer module 220 may be inserted and removed by hand by a user. For example, the transducer module 220 may be inserted and removed from the module receiver 230 manually without the aid of tools or other mechanical devices. As such, the transducer module 220 is not permanently fastened into the module receiver 230 but may not become uncoupled from the module receiver 230 during scanning.

The internal portion 518 of the transducer module 220 may form part of the complementary mechanical connection. The internal portion 518 fits inside of the module receiver 230. Specifically, the module receiver 230 defines a socket 404 which mates with the protrusions (e.g., first protrusion 520 and second protrusion 530) of the transducer module 220. The dashed lines shown in FIG. 4 show the socket 404 of the module receiver 230. The socket 404 includes a first recess 406 and a second recess 408. The first recess 406 is a complementary recess adapted to mate with the first protrusion 520 of the transducer module 220. Specifically, the first recess 406 has face-sharing contact with the first protrusion 520. Additionally, the module receiver 230 may include another protrusion formed by the first recess 406 around an outer perimeter of the module receiver 230. This other protrusion of the module receiver 230 has face-sharing contact with the lip of the first recess 526 of the transducer module 220.

Likewise, the second recess 408 is a complementary recess adapted to mate with the second protrusion 530 of the transducer module 220. The second recess 408 further includes a first standard electrical connector (e.g., first connector 410) which mates with the second standard electrical connector 532 (e.g., second connector) of the transducer module 220 (shown in FIG. 5). As such, the first connector 410 includes two reversed and parallel connectors that mate with the reversed and parallel connectors of the second connector 532 (e.g., first PCI connector 531 and second PCI connector 533). The first connector 410 and the second connector 532 make up the complementary electric connection between the module receiver 230 and the transducer module 220 (e.g., the first connector and the second connector are complementary electrical connectors). Both the first connector 410 and the second connector 532 may be PCI connectors. For example, the first connector 410 may be a PCI slot and the second connector 532 may be a PCI card.

When the transducer module 220 is positioned within the socket 404, the transducer module 220 is secured and mechanically coupled within the socket. In one example, the complementary shapes of the protrusions (e.g., protrusions 520 and 530) and the socket 404 (e.g., recesses 406 and 408) enable the transducer module 220 to be secured in the socket 404 of the module receiver 230 with a press-fit connection. The press-fit connection may mechanically couple the module receiver 230 to the transducer module 220. In this way, when the transducer module 220 is removably and mechanically coupled with the module receiver 230, it is also electrically coupled with the module receiver 230. As a result, the transducer module 220 may acquire volumetric ultrasound data while coupled with the module receiver 230.

Additionally, the first end 502 of the transducer module 220 is able to be coupled to the module receiver 230 in at least two different positions. Specifically, as shown in FIG. 5, the transducer module 220 has inverse mirror symmetry about a plane intersecting the transducer array of the transducer module 220 enabling coupling with the module receiver 230 in a first position or a second position. The plane intersecting the transducer array is defined by the vertical axis 304 and the lateral axis 308. In one example, the second position is rotated 180 degrees with respect to the first position. As described above, the second connector 532 may include two electrical connectors. Similarly, the first connector 410 may include two electrical connectors. As such, each of the two electrical connectors of the second connector 532 couples with a respective electrical connector of the first connector 410. However, upon rotating the transducer module 220 180 degrees with respect to the vertical axis 304, each of the two electrical connectors of the second connector 532 may couple with the opposite electrical connector of the first connector 410.

As introduced above, a transducer module and/or the transducer array may have a unique length (e.g., length 506 shown in FIG. 5), curvature (e.g., curvature radius 514 shown in FIG. 5), number of transducer elements in the transducer array, and/or center frequency of the transducer array. In other examples, the transducer module may include a unique number and/or size of the mechanical focusing elements. The geometrical and transducer array parameters listed above may be selected based on tissues or patients with different tissue density and size.

In one example, an ultrasonic scanning system, such as an FFBU scanning apparatus, may include a plurality of transducer modules. In one example, a user may be provided with a set of transducer modules, each transducer module of the set of transducer modules differing in at least one of the curvature of the transducer module, the length of the transducer module, the number of transducer elements in the transducer array, and/or the center frequency of the transducer array. However, the first end (e.g., first end 502 shown in FIG. 5) of each of the transducer modules in the set (e.g., plurality) of transducer modules has the same configuration as the first end of all the other transducer modules in the set of transducer modules.

For example, a first breast for ultrasound scanning may be larger in width and height than a second breast for ultrasound scanning (the first breast may be of a different patient than the second breast). Thus, a first transducer module used to scan the first breast may have a longer length and/or larger curvature radius than a second transducer module used to scan the second breast. In another example, the tissue of the first breast may be denser than the tissue of the second breast. As a result, the first transducer module used to scan the first breast may have a greater number of transducer elements and/or a higher center frequency than the second transducer module used to scan the second breast. In other examples, a transducer module may be selected from a set of transducer modules based on a required image quality or a type of tissue being imaged. In this way, providing a plurality of transducer modules may increase the versatility of the ultrasound scanning system. As a result, a user may swap out transducer modules having different geometrical and array parameters for different patients or tissues. Further, the transducer module being removably coupled via socket electrical and mechanical connections with the module receiver provides for a modular transducer system. If a transducer module becomes degraded, a user may more quickly and easily replace the degraded module with a non-degraded module in the modular transducer system.

As one embodiment, a system for ultrasonically scanning a tissue sample comprises: an adjustable arm; a scanning assembly attached to the adjustable arm, the scanning assembly including a housing configured to remain stationary during scanning and a module receiver that is configured to translate with respect to the housing during scanning; and a transducer module comprising a transducer array of transducer elements, wherein the transducer module is configured to be removably coupled with the module receiver in order to establish both a mechanical connection and an electrical connection between the module receiver and the transducer module.

The system further comprises a plurality of transducer modules, wherein the transducer module is one of the plurality of transducer modules. Each of the plurality of transducer modules is configured to acquire volumetric ultrasound data while removably coupled with the module receiver. Additionally, each of the plurality of transducer modules is configured to be coupled with the module receiver in at least two different positions. For example, each of the plurality of transducer modules has a symmetry enabling coupling with the module receiver in a first position or a second position that is rotated 180 degrees with respect to the first position. Further, the module receiver and each of the plurality of transducer modules are collectively configured to allow any one of the plurality of transducer modules to be either inserted into the module receiver or removed from the module receiver by hand.

The module receiver includes a first standard electrical connector and each of the plurality of transducer modules includes a second standard electrical connector. In one example, the first standard electrical connector is a PCI connector and the second standard electrical connector is a PCI connector. Each of the plurality of transducer modules has a first end including the first standard electrical connector and a second end including the transducer array of transducer elements, the first end opposite the second end. The second end of a first of the plurality of transducer modules differs from the second end of a second of the plurality of transducer modules in at least one of a curvature of the transducer module, a length of the transducer module, a number of transducer elements in the transducer array, and a center frequency of the transducer array. Additionally, the first end of the first of the plurality of transducer modules has the same configuration as the first end of the second of the plurality of transducer modules.

Further, the housing defines an opening and the system further comprises a membranous sheet disposed across the opening, the transducer module positioned to contact the membranous sheet when the transducer module is attached to the modular receiver.

As another embodiment, an apparatus for ultrasonically scanning a tissue sample comprises: an adjustable arm and a scanning assembly attached to the adjustable arm. The scanning assembly comprises: a housing defining an opening, wherein the housing is configured to remain stationary while scanning; a membranous sheet stretched across the opening of the housing; a module receiver adapted to translate with respect to the housing, the module receiver defining a socket; and a transducer module comprising a plurality of transducer elements, wherein the transducer module and the module receiver are collectively configured to allow for both insertion of the transducer module into the module receiver and removal of the transducer module from the module receiver without the use of tools, and wherein the transducer module is configured to contact the membranous sheet while ultrasonically scanning the tissue sample.

The transducer module is shaped to be secured in the socket with a press-fit connection. Additionally, the transducer module includes a protrusion and the module receiver is shaped to define a complimentary recess that is adapted to mate with the protrusion when the transducer module is positioned in the socket to secure the transducer module in the socket. Further, the transducer module is shaped to define a recess and the module receiver includes a protrusion that is adapted to mate with the recess when the transducer module is positioned in the socket to secure the transducer module in the socket.

The module receiver includes a first connector and the transducer module includes a second connector that is complementary to the first connector. The second connector and the transducer module comprises inverse mirror symmetry about a plane intersecting the transducer array so that the second connector is configured to interface with the first connector in a first position or a second position that is rotated 180 degrees from the first position.

As a further embodiment, a transducer module for a scanning assembly comprises a casing, a transducer array of transducer elements housed in the casing, and a first connector configured to connect with a second connector of a module receiver of the scanning assembly, the transducer module shaped to be secured in a socket of the module receiver with a press-fit connection.

The transducer module is removably coupleable with the module receiver. The transducer module includes a protrusion and the module receiver is shaped to define a complimentary recess that is adapted to mate with the protrusion when the transducer module is positioned in the socket to secure the transducer module in the socket. The first connector may comprise a PCI card and the second connector may comprise a PCI slot. The transducer module is configured to acquire volumetric ultrasound data and send the volumetric ultrasound data to the module receiver via the first connector.

FIGS. 6A and 6B show cross-sections of the transducer module 220. FIGS. 6A and 6B both show the coordinate system 302. Specifically, FIG. 6A shows a schematic 600 of a front cross-section of the transducer module 220 in a plane defined by the vertical axis 304 and the lateral axis 308, while FIG. 6B shows a schematic 650 of a side cross-section of the transducer module 220 in a plane defined by the vertical axis 304 and the horizontal axis 306. As described above, the transducer module 220 includes the first end 502 configured to connect to a module receiver. The first end 502 includes the standard electrical connector 532, such as a PCI connector, positioned in the first protrusion 520 of the transducer module 220. The transducer module also includes the second end 504 configured to contact a patient tissue during scanning (via a membrane in some examples). Positioned in the transducer module 220, near the second end 504, are a plurality of transducer elements 602 forming a transducer array. As illustrated, the transducer elements 602 are arranged in groups that are equally spaced apart from each other across the entire length (e.g., length 506 shown in FIG. 5) of the second end 504. However, other configurations for the transducer elements 602 are possible. For example, the transducer elements may be arranged individually. While a single row of transducer elements 602 are illustrated in FIG. 6A, it is to be understood that at least in some embodiments, additional transducer elements may extend across a width of the transducer module 220 in order to form an array of transducer elements.

The transducer elements 602 may be positioned a distance from the surface (e.g., contact surface) of the second end 504 of the transducer module 220. This distance may be the same for all transducer elements, such that if the surface of the transducer module is curved, the array of transducer elements 602 is also curved. However, in other embodiments, this distance may differ for transducer elements positioned in different regions of the transducer module 220. For example, the transducer elements 602 may be arranged in a straight row without curvature that extends across a length of the transducer module 220. If the surface of the second end 504 is curved, the transducer elements 602 located along each side of the transducer module 220 may be spaced a farther distance from the surface than the transducer elements located in the center of the transducer module 220. Additionally, the array may include one or more mechanical focusing elements, such as acoustic lenses, along the length of the transducer module 220 and positioned between the transducer elements 602 and the surface of the second end 504.

Further, the transducer elements 602 may be positioned across the entire length and width of the transducer module 220, or the transducer elements 602 may be positioned across only a portion of the length and/or width of the transducer module 220. For example, the transducer elements 602 may extend only across a central area of the transducer module.

Each transducer element is configured to transmit and receive ultrasound waves to acquire image data of the tissue being scanned. In order to send the image data to a processor for image processing, each transducer element may be connected to the standard electrical connector 532 via a cable or other connection. In this way, the raw image data collected by the transducer module may be sent to an image processor via the connection with the module receiver.

Further, in some embodiments, a plurality of sensors 604 may be distributed across the transducer module 220. The sensors 604 may include one or more pressure sensors and/or one or more temperature sensors. The sensors 604 may be distributed evenly across the transducer module 220. In one example, the sensors 604 are positioned proximate to the surface of the second end 504 of the transducer module 220. The output from the sensors 604 may be stored in the memory 224 of the transducer module 220. In one example, the number of pressure sensors and/or temperature sensors may be in a range of six to ten. For example, the transducer module 220 may include ten pressure sensors 604. In another example, the transducer module 220 may include ten sensors 604, the ten sensors 604 including eight pressure sensors and two temperature sensors. In this way, the transducer module 220 may include different numbers of pressure and temperature sensors.

FIG. 6B illustrates a side cross-section of the transducer module 220 including the first protrusion 520 extending out from the external portion 516 of the transducer module 220. As shown in FIG. 6B, the first protrusion 520 includes tapered front walls 608, e.g., the front walls 608 of the first protrusion 520 are angled with respect to the front walls 610 of the external portion 516 at an angle 612. In one example, angle 612 may be 1°. In another example, angle 612 may be 2°, or another suitable angle. The tapering of the first protrusion 520 may allow for a more secure connection between the transducer module 220 and the module receiver 230, for example.

First protrusion 520 includes a standard electrical connection comprising two PCI connectors, first PCI connector 531 and second PCI connector 533. Each PCI connector may be connected to a row of transducer elements. As shown, the transducer module 220 includes the plurality of transducer elements 602 discussed above with respect to FIG. 6A, arranged in a first row, and a second plurality of transducer elements 606 arranged in a second row. The first row of the plurality of transducer elements 602 may be connected (e.g., electrically coupled) to the first PCI connector 531 while the second row of transducer elements 606 may be connected (e.g., electrically coupled) to the second PCI connector 533. However, other configurations are possible. For example, first PCI connector 531 and second PCI connector 533 may each be connected to multiple rows of transducer elements.

As one embodiment, a transducer module for an ultrasound imaging system comprises a casing configured to fit into a module receiver of the ultrasound imaging system; an array of transducer elements; and a non-transitory memory configured to store at least one of usage data and specification data for the transducer module.

The non-transitory memory may be configured to store both usage data and specification data. The non-transitory memory may be automatically updated in response to activation of the transducer module. The non-transitory memory may be configured to store at least one of total time scanning, number of scans, time since last service, and types of scans performed. The non-transitory memory may be configured to store at least one of an array geometry, a number of elements in the array, or an identification number of the transducer module.

The transducer module may further comprise a plurality of pressure sensors distributed across the transducer module. The plurality of pressure sensors may be configured to send to a processor output indicative of a pressure distribution across the transducer module when the transducer module is positioned on a tissue to be scanned by the transducer module. The non-transitory memory may be configured to store usage data including the output of the plurality of pressure sensors.

As another embodiment, an apparatus for ultrasonically scanning a tissue sample comprises an adjustable arm and a scanning assembly attached to the adjustable arm, the scanning assembly comprising: a housing configured to define an opening; a module receiver adapted to translate across the opening of the housing; a transducer module adapted to be removably coupled with the module receiver; a plurality of pressure sensors positioned in the transducer module; and a memory attached the transducer module, the memory configured to store at least one of usage data and transducer module specification data, the usage data based at least in part on output from the plurality of pressure sensors.

The apparatus may further comprise a membranous sheet attached to the housing and disposed across the opening of the housing. The apparatus may further comprise a processor configured to receive output from the plurality of pressure sensors and notify a user if a distribution of pressure across the transducer module is unequal.

The memory may be configured to record a number of imaging procedures performed by the transducer module. The memory may be configured to record a number of imaging procedures performed by the transducer module since last service. The memory may be configured to store identifying information about the transducer module. The memory may comprise EEPROM in one example. In another example, the memory may comprise RAM.

While the above-described non-transitory memory configured to store usage and/or specification data is described with respect to the transducer module configured to be removably coupled to a module receiver, the memory may be positioned in other transducer configurations, such as in a hand-held scanner probe including a nose piece. As an example, a transducer module for an automated breast imaging system comprises a transducer nose piece including an acoustic lens; a plurality of transducer elements connected to the transducer nose piece; a memory; and a connector configured to attach to a scanning assembly of the automated breast imaging system.

The memory may be configured to store identifying information about the transducer module. The memory may be configured to store information about the number of transducer elements. The memory may be configured to store information about the geometry of the transducer elements. The memory may be configured to store service information for the transducer module. The memory may be configured to store information about the number of scans performed with the transducer module. The memory may comprise read-write memory. The memory may comprise EEPROM memory.

Figure 7:
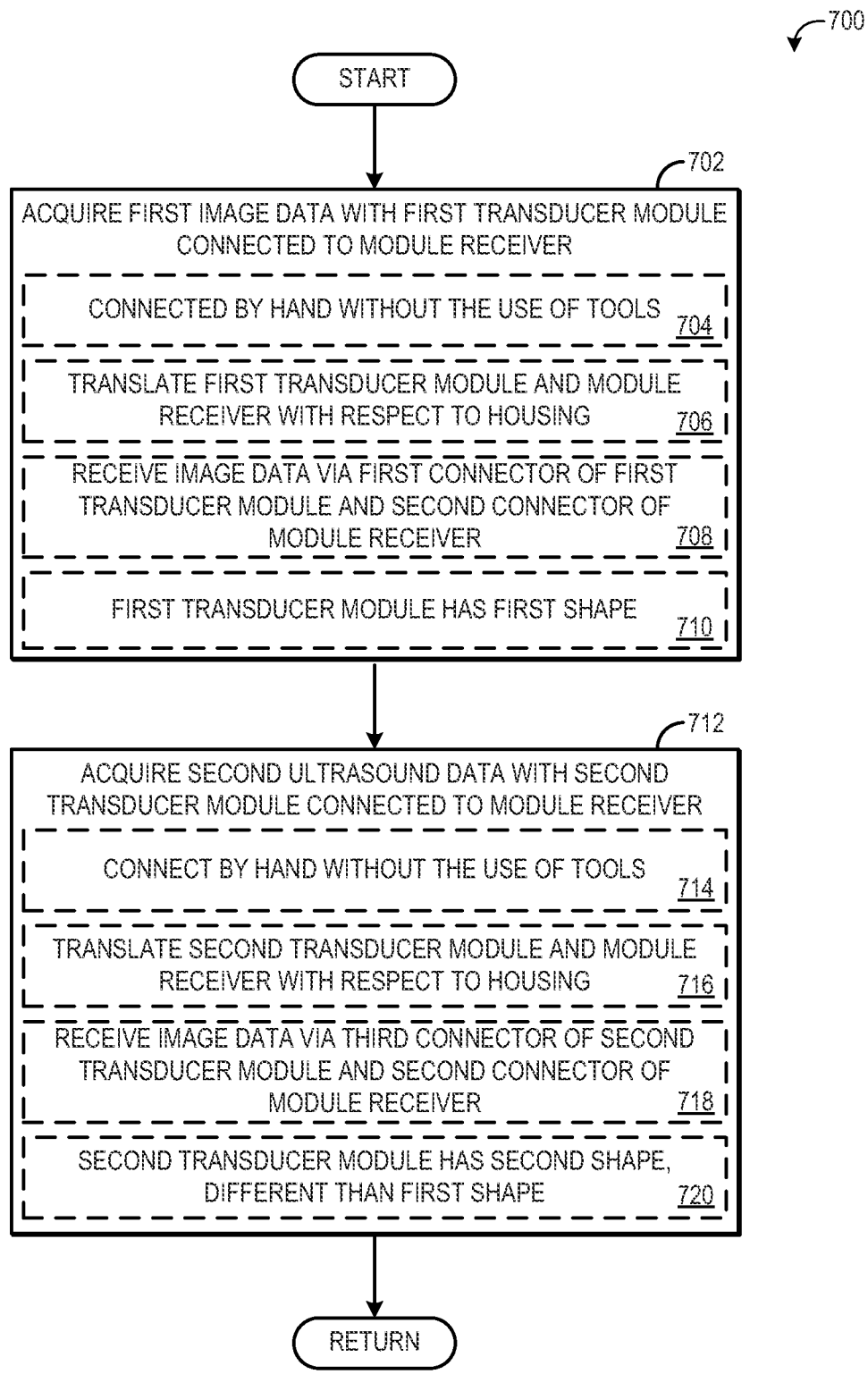
FIG. 7 is a flow chart illustrating a method for acquiring image data according to embodiment of the invention.

Turning now to FIG. 7, a method 700 for acquiring ultrasound data is illustrated. Method 700 may be performed using the scanning apparatus 102 of FIG. 1 including a plurality of transducer modules, such as transducer module 220 of FIGS. 2-6B, configured to connect to a module receiver of the scanning apparatus.

At 702, method 700 includes acquiring first image data with a first transducer module connected to a module receiver. As explained previously, a scanning assembly may include a module receiver configured to translate with respect to a stationary housing in order to acquire ultrasound image data of a patient tissue. A modular transducer including a transducer array having a plurality of transducer elements is configured to connect to the modular receiver and thus translates with the module receiver during scanning. The first transducer module may be one of a plurality of transducer modules, each shaped to connect with the module receiver.

The first transducer module may be connected into the module receiver by hand without the use of tools, as indicated at 704. The first transducer module may include a first connector configured to connect with a second connector of the module receiver in order to establish both a mechanical connection and an electrical connection between the transducer module and the module receiver. The transducer module and module receiver may connect via a suitable mechanism. In one example, the module receiver defines a socket, and the transducer module is shaped to be secured into the socket with a press-fit connection. The transducer module may include a protrusion that is adapted to mate with a recess of the module receiver. In another example, the transducer module may define a socket, and the module receiver may be shaped to be secured in the socket with a press-fit connection. The module receiver may include a protrusion adapted to mate with a recess of the transducer module.

Acquiring the image data from the first transducer module further includes translating the first transducer module and module receiver with respect to the housing, as indicated at 706. The module receiver may be moved via a motor of the module receiver or via another suitable mechanism. The motor may be activated (as well as the transducer elements of the transducer module) in response to a user input instructing the scanning assembly to acquire the image data.

Acquiring the image data further includes receiving image data from the first transducer module via a first connector of the first transducer module and a second connector of the module receiver, as indicated at 708. The first connector of the first transducer module may be a PCI card, and the second connector of the module receiver may be a PCI slot. The received image data may include ultrasound echoes of ultrasound waves transmitted by the transducer elements of the first transducer module. The ultrasound echoes may be sent to an image processor to be processed into an image of the tissue. In some examples, the image data may include volumetric ultrasound data.

Further, as indicated at 710, the first transducer module may have a first shape. The first shape of the first transducer module may be a shape that is selected based on one or more parameters of the tissue being imaged. For example, the first transducer module may be shaped to image a first breast. The shape of the first transducer module may include a particular length, geometry of the transducer array, number of transducer elements, or other configuration that is optimized to collect image data of the first breast.

At 712, method 700 includes acquiring second image data with a second transducer module connected to the module receiver. The image data may include volumetric ultrasound data. To acquire the image data, the transducer elements of the second transducer module convert energy into ultrasound waves and also detect the ultrasound waves reflected off the tissue. Similar to the first transducer module, the second transducer module may be connected to the module receiver by hand without the use of tools, as indicated at 714. The second transducer module may connect with the module receiver in the same location as the first module receiver, according to the same connection mechanism. For example, the second transducer module may include a protrusion adapted to mate with the recess of the of the module receiver. The second transducer module may include a connector, similar to the first connector of the first transducer module, which connects with the second connector of the module receiver.

When the second transducer module is connected with the module receiver, the first transducer module is not connected to the module receiver. That is, the module receiver is configured to connect to only one transducer module at a time. As such, before the second transducer module is connected to the module receiver, the first transducer module is disconnected from the module receiver. The first transducer module may be disconnected from the module receiver by hand without the use of tools. The first transducer module may be disconnected in order to service the first transducer module or replace the first transducer module with the second transducer module, for example if the first transducer module is degraded or broken. Additionally or alternatively, the first transducer module may be disconnected if the first transducer module is not configured to optimally image a subsequent tissue, as explained further below.

Acquiring the image data from the second transducer module further includes translating the second transducer module and module receiver with respect to the housing, as indicated at 716. The module receiver may be moved via a motor of the module receiver or via another suitable mechanism. The motor may be activated (as well as the transducer elements of the transducer module) in response to a user input instructing the scanning assembly to acquire the image data.

Acquiring the image data further includes receiving image data from the second transducer module via a third connector of the second transducer module and the second connector of the module receiver, as indicated at 718. The third connector of the second transducer module may be a PCI card, and the second connector of the module receiver may be a PCI slot. The received image data may include ultrasound echoes of ultrasound waves transmitted by the transducer elements of the first transducer module. The ultrasound echoes may be sent to an image processor to be processed into an image of the tissue. In some examples, the image data may include volumetric ultrasound data.

Further, as indicated at 720, the second transducer module may have a second shape that is different than the first shape of the first transducer module. The second shape of the second transducer module may be a shape that is selected based on one or more parameters of the tissue being imaged. For example, the second transducer module may be shaped to image a second breast. The shape of the second transducer module may include a particular length, geometry of the transducer array, number of transducer elements, or other configuration that is optimized to collect image data of the second breast.

In this way, a transducer module may be connected to a module receiver that is part of a scanning assembly configured to acquire image data of a tissue. The transducer module, which includes plurality of transducer elements configured to emit and receive ultrasound waves, may be connected to the module receiver by hand by an ultrasound technician or other end user without the use of tools or specialized equipment. As such, when the transducer module is degraded or breaks, a new transducer module may be inserted into the scanning assembly, alleviating the need for an outside repairperson to service the scanning assembly.

Further, in some examples, multiple transducer modules may be available for use, each having differing characteristics or specifications optimized for different sized tissues and/or tissues having differing densities. For example, a first transducer module may be a first length and/or curvature that is configured to acquire images of a relatively small breast. A second transducer module may be a second length, longer than the first length, and/or of a different curvature than the first transducer module that is configured to acquire images of a relatively larger breast. Thus, different transducer modules may be used for different patients and different tissues.

Therefore, in one embodiment, a method of acquiring ultrasound data comprises acquiring first ultrasound data from a first transducer module connected into a module receiver attached to a housing, the first ultrasound data acquired by automatically translating both the module receiver and the first transducer module with respect to the housing and receiving the first ultrasound data from the first transducer module via a first connector of the first transducer module and a second connector of the module receiver. The method further includes acquiring second ultrasound data from a second transducer module connected into the module receiver, the second ultrasound data acquired by automatically translating both the module receiver and the second transducer module with respect to the housing, and receiving the second ultrasound data from the second transducer module via a first connector of the second transducer module and the second connector of the module receiver.

Acquiring the first ultrasound data may comprise acquiring the first ultrasound data of a first breast, and acquiring the second ultrasound data may comprise acquiring the second ultrasound data of a second breast. In some examples, acquiring the first ultrasound data of the first breast comprises acquiring the first ultrasound data with the first transducer module shaped to fit the first breast, and acquiring the second ultrasound data of the second breast comprises acquiring the second ultrasound data with the second transducer module shaped to fit the second breast. In an example, the first transducer module is shaped differently than the second transducer module.

Additionally or alternatively, the first transducer module may comprise a different specification than the second transducer module. For example, the first transducer module may have a different length than a second transducer module, a different number of transducer elements than the second transducer module, a different transducer element geometry than the second transducer module, emit ultrasound waves of a different frequency than the second transducer module, and/or have additional parameters that are different from the second transducer module.

The connection between the first transducer module and the module receiver comprises a physical and electrical connection between the first transducer module and the module receiver. For example, the module receiver may hold the first transducer module in position via a mechanical connection (such as a press-fit connection). Further, the image data acquired by the first transducer module may be sent to an image processor via an electrical connection (such as a PCI connection) between the first transducer module and the module receiver.

If the first transducer module is degraded or if a transducer module of a different specification is desired, the first transducer module may be replaced by the second transducer module. The connection between the second transducer module and the module receiver comprises a physical and electrical connection between the second transducer module and the module receiver. For example, the module receiver may hold the second transducer module in position via a mechanical connection (such as a press-fit connection). Further, the image data acquired by the second transducer module may be sent to an image processor via an electrical connection (such as a PCI connection) between the second transducer module and the module receiver.

Acquiring first ultrasound data from the first transducer module may comprise acquiring first ultrasound data from the first transducer module and not the second transducer module, and acquiring second ultrasound data from the second transducer module may comprise acquiring second ultrasound data from the second transducer and not the first transducer. The module receiver may be configured to connect to only one transducer module at a time.

Another embodiment for a method of acquiring ultrasound data comprises connecting a first transducer module into a module receiver attached to a housing and acquiring first ultrasound data by automatically translating both the module receiver and the first transducer module with respect to the housing. The method further comprises disconnecting the first transducer module from the module receiver, connecting a second transducer module to the module receiver, and acquiring second ultrasound data by automatically translating both the module receiver and the second transducer module with respect to the housing. In some examples, acquiring the first ultrasound data and acquiring the second ultrasound data both comprise acquiring volumetric ultrasound data.

Figure 8:
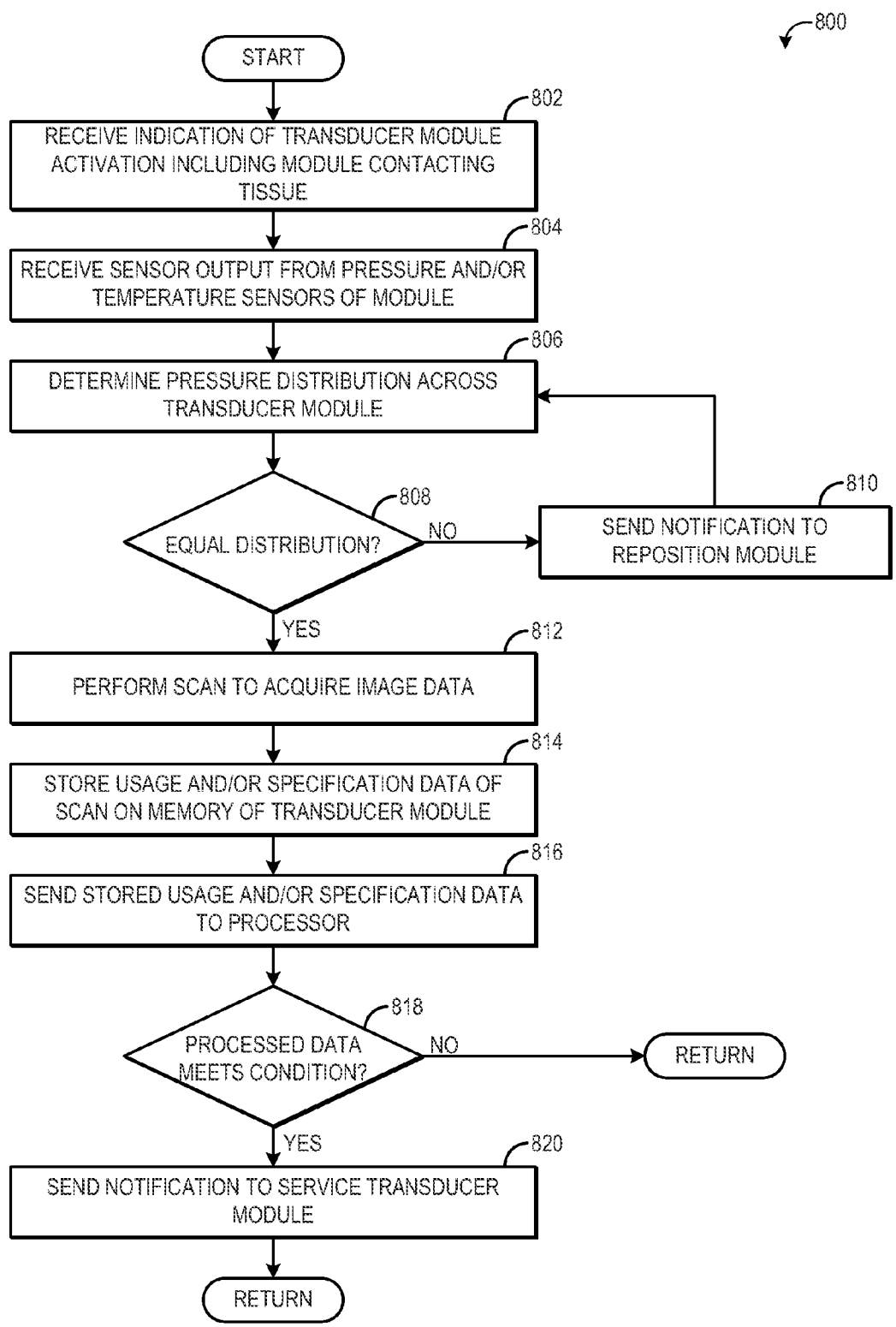
FIG. 8 is a flow chart illustrating a method for acquiring image data according to another embodiment of the invention.

FIG. 8 is a flow chart illustrating a method 800 for acquiring ultrasound imaging data according to another embodiment of the present disclosure. Method 800 may be performed using the scanning apparatus 102 of FIG. 1 including a transducer module, such as transducer module 220 of FIGS. 6A and 6B, configured to connect to a module receiver of the scanning apparatus and including a memory for storing usage and/or specification data of the transducer module.

At 802, method 800 includes receiving an indication of a transducer module activation including the transducer module contacting a tissue. For example, an ultrasound technician, doctor, or other user may position the scanning assembly on a patient's tissue and enter an input to the scanning assembly instructing the scanning assembly to initiate scanning to acquire imaging data of the tissue. When the input is received, the module receiver (and attached transducer module) will be translated with respect to the scanning assembly housing to acquire ultrasound images of the tissue using ultrasound waves emitted by the transducer module. To acquire the images, the transducer module may be in contact with the tissue (via a membranous sheet in some examples).

At 804, method 800 includes receiving sensor output from one or more pressure and/or temperature sensors of the transducer module. As explained previously with respect to FIG. 6A, the transducer module may include a plurality of pressure sensors and one or more temperature sensors. The pressure and/or temperature sensors may be distributed across the transducer module at an end of the module configured to contact the patient tissue.

At 806, method 800 includes determining the pressure distribution across the transducer module based on the output from the pressure sensors. For example, the plurality of pressure sensors may be evenly distributed across the surface of the transducer module such that the pressure or force exerted on the imaged tissue by the transducer module may be measured by the pressure sensors. At 808, it is determined if the pressure distribution across the transducer module is substantially equal. A substantially equal pressure distribution may include each pressure sensor measuring a pressure that is within a threshold range, such as within 5% of an average pressure of all the pressure sensors.

If the pressure sensor output indicates that the pressure distribution is not substantially equal, such as if one pressure sensor is measuring a pressure that is significantly greater than the remaining pressure sensors, it may indicate that the transducer module is not contacting the patient tissue in an equal manner, and that one portion of the transducer module may be contacting the tissue with greater force than the remaining portions of the transducer module. This unequal contact may result in reduced-quality images. For example, unequal contact may produce uneven images that may not show constant tissue properties. As a result, breast lesions corresponding to areas of lighter contact may not be found. As such, if the pressure distribution is not equal, method 800 proceeds to 810 to send a notification to the user of the scanning assembly to reposition the transducer module, for example by repositioning the entire scanning assembly, until an equal pressure distribution is reached. The notification may be displayed on a user interface of a display coupled to the scanning assembly, for example. Method 800 then loops back to 806 to continue to determine the pressure distribution across the transducer module.

If the pressure distribution is equal, method 800 proceeds to 812 to perform a scan to acquire image data. As explained above with respect to FIG. 7, performing the scan includes translating the module receiver and transducer module with respect to the housing to acquire image data (e.g., ultrasound echoes) of each region of the tissue to be imaged. The image data may be sent from the transducer module to an image processor via the module receiver to process the raw image data into images of the tissue.

During the scan, usage and/or specification data of the scan may be stored on the memory of the transducer module, as indicated at 814. The usage data may include information relating to how the transducer module is being used. For example, each time the transducer module is activated, the memory may be updated to reflect the total amount of times the transducer module is activated (e.g., used). Further, the total amount of time the transducer module is activated may also be stored. Other information that may be stored includes the amount of time the transducer module spends actually moving during the scan, the pressure placed on the patient tissue during the scan by the transducer module (determined based on the output of the pressure sensors, for example), the temperature of the transducer module during the scan (determined based on the output of temperature sensors, for example), and other information. While the usage data as described herein is based on output from the same pressure sensors used to determine the pressure distribution across the transducer module prior to scanning, the output from the pressure sensors may be averaged or otherwise filtered before being stored as part of the usage data. In contrast, the output from the pressure sensors used to determine the pressure distribution prior to scanning may be the instantaneous pressure received at that time. As such, the pressure distribution determined prior to scanning may be based on the instantaneous pressure output while the pressure information stored in the memory as part of the usage data may be based on an average pressure output over the duration of the scanning.

The specification data of the transducer module may include identifying information of the module (such as serial number) and/or information relating to the parameters of the transducer module, such as the number of transducer elements, the geometry of the transducer elements, the wavelength of the ultrasound waves emitted by the transducer, curvature radius of the transducer module, and other parameters.

The usage and specification data may be stored in a suitable memory of the transducer module. In one example, the usage and specification data may be stored in EEPROM, so that the data is not erased when the transducer module is powered down. Further, the memory may be configured so that an end user cannot erase the contents of the memory.

At 816, the stored usage and specification data is sent to a processor. The processor may be located on the transducer module or it may be located remotely from the transducer module. In one example, the processor may be located on the scanning apparatus, such as in the scanning processor located in the frame of the scanning assembly, as described above with respect to FIG. 2. In another example, the processor may be located remotely from the scanning apparatus, and the memory may be read by the processor when the transducer module is removed from the scanning assembly. In still further examples, the data may be sent to a remote processor via a network.

The usage and specification data may be usable by the processor to determine if the data meets one or more conditions relative to a threshold. Specifically, the usage data may be usable by the processor to determine if the transducer module has been activated a threshold number of times, if the transducer module has been translated across the housing of the scanning assembly (e.g., if the transducer module has moved) a threshold amount of time, if the temperature of the transducer module has reached a threshold temperature or spent a threshold amount of time above a particular temperature, or other conditions relative to other thresholds. The thresholds to which the usage data are compared may be based on suitable factors. For example, the threshold number of activations that the transducer module can reach before being serviced may be based on an average rate of degradation of the transducer module. The average rate of degradation of the transducer module may be determined based on the specification of the transducer module (e.g., make and model of the module), which may also be stored in the memory, as explained below. Based on the data, the processor may determine if the transducer module should be serviced, repaired, or replaced.

In an embodiment, usage data relating to the pressure on the transducer module may be used by the processor to determine if the transducer module is in need of service or replacement. For example, if the pressure distribution across the transducer during scanning is uneven for multiple scanning events, it may indicate that the surface of the module is uneven, or it may indicate that some of the transducer elements are degraded (e.g., if the transducer elements are degraded in a region of the module, the user may place additional pressure on the module at that region to acquire a high-quality image). The pressure information utilized in the usage data to determine if the transducer module is degraded or in need of servicing may be based on the same pressure sensors used to determine if the pressure distribution across the transducer module is equal, as described above.

Additionally, the specification data, in conjunction with the usage data, may be usable by the processor to determine if the transducer module should be serviced or replaced. For example, a first transducer module having a first specification may need to be serviced after a threshold number of activations (such as after 300 activation events), while a second, different transducer module having a different specification may need to be serviced after a different number of activations, such as after 400 activation events. As such, the specification data may include the number of times the transducer can be activated before service is indicated, or the specification data may include identifying information that the processor can use to determine the number of recommended activations before service, via communication with a remote service, for example.

Accordingly, at 818, method 800 determines if the processed usage and/or specification data meets a condition relative to a threshold. As explained above, the condition relative to the threshold may include a threshold number of activations being reached, a threshold amount of time spent performing scans being reached, a threshold temperature being reached, a threshold pressure being reached, or other suitable condition. If the data does not indicate the condition relative to the threshold has been reached, method 800 returns. If the data does indicate the condition relative to the threshold has been reached, method 800 proceeds to 820 to send a notification to service the transducer module. The notification may include displaying a notification to a user on a user interface of the scanning apparatus, or it may include setting a diagnostic code (stored in the memory of the transducer module) that may be read by a repairperson during a subsequent servicing event. Method 800 then returns.

Thus, the method described above provides for a method for a scanning assembly configured to image a tissue sample. The method comprises during a scanning procedure performed by a transducer module of the scanning assembly, storing usage data on a non-transitory memory of the transducer module, the usage data defining one or more parameters of the transducer module, and sending the usage data to a processor, the usage data usable by the processor to notify a user to service the transducer module when the usage data meets a condition relative to a threshold.

In one example, the usage data comprises a number of scans performed by the transducer module, and the usage data is usable by the processor to notify the user to service the transducer module when the number of scans performed by the transducer module reaches a threshold number. In another example, the usage data comprises a total scanning time of the transducer module, and the usage data is usable by the processor to notify the user to service the transducer module when a total scanning time of the transducer module reaches a threshold time. In a further example, the usage data comprises pressure and temperature profiles of the transducer module based on output received from at least one pressure sensor and at least one temperature sensor of the transducer module.

In this way, various parameters of the transducer module may be tracked and stored in a memory of the transducer module as usage and specification data. Then, the usage and specification data may be periodically read by a processor to determine if the usage and specification data indicate that the transducer module is in condition for a service, repair, or replacement. The data stored in the memory may be remain intact even if the transducer module loses power or is moved to a different scanning apparatus.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An apparatus for ultrasonically scanning a tissue sample, comprising:
   an adjustable arm;
   a scanning assembly attached to the adjustable arm, the scanning assembly comprising:
      a housing configured to define an opening;
      a module receiver including a motor for translating the module receiver across the opening of the housing; and
      a transducer module adapted to be removably coupled with the module receiver, the transducer module comprising:
         a plurality of transducer elements forming a transducer array;
         a plurality of pressure sensors distributed across the transducer module;
         a memory; and
         a processor configured to receive output from the plurality of pressure sensors and execute non-transitory instructions stored in the memory for:
            determining usage data of the transducer module based at least in part on pressure data, the pressure data based on the received output from the plurality of pressure sensors;
            storing the determined usage data in the memory; and
            sending a notification to a user to service the transducer module in response to determining the stored usage data meets a condition relative to a threshold.

2. The apparatus of claim 1, wherein the non-transitory instructions further include instructions for determining from the stored usage data if a pressure distribution across the transducer module during scanning is uneven for multiple scanning events and, in response to the determination of uneven scanning for multiple scanning events, sending the notification to the user to service the transducer module, and wherein the apparatus further comprises a membranous sheet attached to the housing and disposed across the opening of the housing.

3. The apparatus of claim 1, wherein the non-transitory instructions further include instructions for determining a distribution of pressure across the transducer module based on the output from the plurality of pressure sensors, sending a signal to initiate scanning with the scanning assembly in response to the determined distribution of pressure across the transducer module being substantially equal, such that each pressure sensor of the plurality of pressure sensors measures a pressure that is within a threshold range of an average pressure of all pressure sensors in the plurality of pressure sensors, and notifying the user if the determined distribution of pressure across the transducer module is not substantially equal prior to scanning.

4. The apparatus of claim 1, wherein the memory is configured to record a number of imaging procedures performed by the transducer module and wherein the usage data is based on the received output from the plurality of pressure sensors during scanning the tissue sample.

5. The apparatus of claim 1, wherein the pressure data includes one or more of an average output from all pressure sensors of the plurality of pressure sensors and a pressure distribution across the transducer module.

6. The apparatus of claim 1, wherein the memory is configured to store identifying information about the transducer module and wherein the memory is configured to record a number of imaging procedures performed by the transducer module since last service.

7. The apparatus of claim 1, wherein the memory comprises EEPROM.

8. The apparatus of claim 1, wherein the memory comprises RAM memory.

9. An apparatus for ultrasonically scanning a tissue sample, comprising:
   an adjustable arm;
   a scanning assembly attached to the adjustable arm, the scanning assembly comprising:
      a housing configured to define an opening;

a module receiver including a motor for translating the module receiver across the opening of the housing; and a transducer module adapted to be removably coupled with the module receiver, the transducer module comprising:
 a plurality of transducer elements forming a transducer array;
 a plurality of pressure sensors distributed across the transducer module;
 a memory; and
 a processor configured to receive output from the plurality of pressure sensors and execute non-transitory instructions stored in the memory for:
  determining a distribution of pressure across the transducer module based on the received output from the plurality of pressure sensors;
  sending a signal to initiate scanning with the scanning assembly in response to the determined distribution of pressure across the transducer module being substantially equal, such that each pressure sensor of the plurality of pressure sensors measures a pressure that is within a threshold range of an average pressure of all pressure sensors in the plurality of pressure sensors; and
  during scanning, determining usage data of the transducer module based at least in part on pressure data, the pressure data based on the received output from the plurality of pressure sensors and storing the determined usage data in the memory.

10. The apparatus of claim 9, wherein the non-transitory instructions further include instructions for notifying a user if the determined distribution of pressure across the transducer module is not substantially equal prior to scanning.

11. The apparatus of claim 9, wherein the non-transitory instructions further include instructions for sending a notification to a user to service the transducer module in response to determining the stored usage data meets a condition relative to a threshold.

* * * * *